US012616801B2

(12) United States Patent
Condon et al.

(10) Patent No.: US 12,616,801 B2
(45) Date of Patent: May 5, 2026

(54) PHLEBOTOMY AID DEVICE

(71) Applicant: Christopher J. Lutz, Sudbury, MA (US)

(72) Inventors: Terry R Condon, Shrewsbury, MA (US); John W. Harding, Shrewsbury, MA (US)

( * ) Notice: Subject to any disclaimer, the term of this patent is extended or adjusted under 35 U.S.C. 154(b) by 1220 days.

(21) Appl. No.: 17/517,309

(22) Filed: Nov. 2, 2021

(65) Prior Publication Data

US 2022/0134024 A1 May 5, 2022

Related U.S. Application Data

(60) Provisional application No. 63/109,041, filed on Nov. 3, 2020.

(51) Int. Cl.
A61M 5/42 (2006.01)

(52) U.S. Cl.
CPC ..... A61M 5/425 (2013.01); *A61M 2205/3368* (2013.01); *A61M 2205/3673* (2013.01); *A61M 2205/8206* (2013.01); *A61M 2210/083* (2013.01)

(58) Field of Classification Search
None
See application file for complete search history.

(56) References Cited

U.S. PATENT DOCUMENTS

| | | | | |
|---|---|---|---|---|
| 5,861,610 A | * | 1/1999 | Weiss | G05D 23/24 |
| | | | | 219/505 |
| 10,272,211 B1 | * | 4/2019 | Cooke | A61M 5/427 |
| 2002/0104837 A1 | * | 8/2002 | Rock | D03D 15/283 |
| | | | | 219/545 |
| 2009/0177184 A1 | * | 7/2009 | Christensen | A61H 9/0057 |
| | | | | 604/113 |
| 2010/0241200 A1 | * | 9/2010 | Bruder | A61F 7/02 |
| | | | | 607/114 |
| 2011/0233193 A1 | * | 9/2011 | Cheng | H05B 3/36 |
| | | | | 219/549 |
| 2012/0078223 A1 | * | 3/2012 | Spiegel | A61F 7/034 |
| | | | | 604/113 |
| 2012/0273479 A1 | * | 11/2012 | Kim | H05B 3/342 |
| | | | | 219/494 |
| 2015/0083705 A1 | * | 3/2015 | Cronn | H05B 3/347 |
| | | | | 219/549 |

\* cited by examiner

*Primary Examiner* — Jay B Shah
(74) *Attorney, Agent, or Firm* — Armis IP Law, LLC

(57) ABSTRACT

A phlebotomy aid provides a capability to expand circulatory members for emphasizing venous appearance and accessibility on an epidermal surface. A warming sheath or sleeve extends over a patient forearm for introducing a thermal source adjacent to a patient blood vessel for emphasizing the vein appearance on the epidermal surface. A beating element in the sleeve is powered and controlled by a low voltage circuit for controlled thermal introduction for mitigating discomfort from overheating and eliminating proximity of potentially harmful electrical exposure.

20 Claims, 4 Drawing Sheets

PHLEBOTOMY AID DEVICE

RELATED APPLICATIONS

This patent application claims the benefit under 35 U.S.C. § 119(e) of U.S. Provisional Patent Application Nos. 63/109, 041, filed Nov. 3, 2020, entitled "PHLEBOTOMY AID DEVICE," incorporated herein by reference in entirety

BACKGROUND

Human blood has been found to be an effective indicator of many health parameters. Analysis of blood chemistry is often performed as part of routine medical examinations and also as a screening and diagnostic medium for investigation of more specific medical conditions and determination of appropriate treatment. Phlebotomy is a medical field that relates to therapeutic intervention in a circulatory member for accessing patient bloodflow, typically initiated via a hypodermic needle for piercing an epidermal surface to access a closely located blood vessel just beneath the surface. Such access is significant for both withdrawal of blood for analysis and introduction of fluidic medicine through intravenous lines for intervention.

SUMMARY

A phlebotomy aid device provides a capability to expand circulatory members (typically veins) for emphasizing venous appearance and accessibility on an epidermal surface. A warming sheath or sleeve extends over a patient forearm for introducing a thermal source adjacent to a patient blood vessel for emphasizing the vein appearance on the epidermal surface. A beating element in the sleeve is powered and controlled by a low voltage circuit for controlled thermal introduction for mitigating discomfort from overheating and eliminating proximity of potentially harmful electrical exposure. Introduction of gently controlled warmth induces physiologic changes in the forearm to expand the vein, facilitate bloodflow and pressure, and emphasize the appearance of the vein, facilitating accurate needle penetration as the vein "stands out" on the epidermal surface and becomes more receptive to a needle puncture. A disposable liner sized slightly smaller than the sleeve interior allows inexpensive use with multiple patients in succession by providing single-use liners to each patient.

Configurations herein are based, in part, on the observation that needle insertions are often routinely undertaken by general nursing staff or patient technicians that are not phlebotomy specialists. Unfortunately, conventional phlebotomy practices suffer from the shortcoming that they tend to result in multiple needle insertions ("pokes") due to an inability to accurately insert the hypodermic needle in a manner that establishes effective fluidic communication with the vein. Typically a nurse is afforded two attempts to "hit" a vein, and if unsuccessful, an escalation protocol elevates the task to more experienced staff. The resulting patient discomfort from multiple needle punctures is substantial. Accordingly, configurations herein substantially overcome the above described shortcomings by providing a phlebotomy aid that enhances appearance and texture of veins and surrounding tissue to allow proper needle insertion into the vein upon a first insertion attempt.

The phlebotomy aid device as disclosed herein includes an elongated flexible sleeve having an opening, in which the flexible sleeve defines a receptacle adapted for receiving a human forearm for warming prior to a blood drawing procedure. A thermal element is attached to or integrated within the sleeve for heating a volume within the receptacle, and a power supply connects to the thermal element for energizing the thermal element. The flexible sleeve, in an example configuration, is constructed from opposed flexible panels attached at a seam extending partially around a perimeter of the flexible panels, and the opening is defined by an absence of the seam for defining the opening. The phlebotomy aid device takes the form of a glove or mitten that fits over the patients forearm up to the elbow region, and gently heats the forearm (the typical insertion site for most routine phlebotomy procedures) to cause the veins to "stand out" for facilitated needle insertion.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations presented below show examples of the phlebotomy aid device for warming a forearm or other insertion site for emphasizing vascular features and facilitating percutaneous insertions, typically needles for IV, blood draw and medication introduction. Other configurations may be apparent from the examples presented below.

The phlebotomy aid device leverages the principle that the presence of a gentle warmth increases bloodflow to the general forearm region, creating a greater pressure in the vein that causes it to expand slightly and become more turgid and stiff to accept a puncture. Surrounding tissue may also stiffen slightly from increased blood flow in the capillaries of the tissue. The overall effect is a vein that is more visible for access, and is more rigid to withstand the pressure of a needle puncture, rather than a "softer" vein that tends to deform and move aside in response to the insertion pressure of an impending needle.

Figure 1:
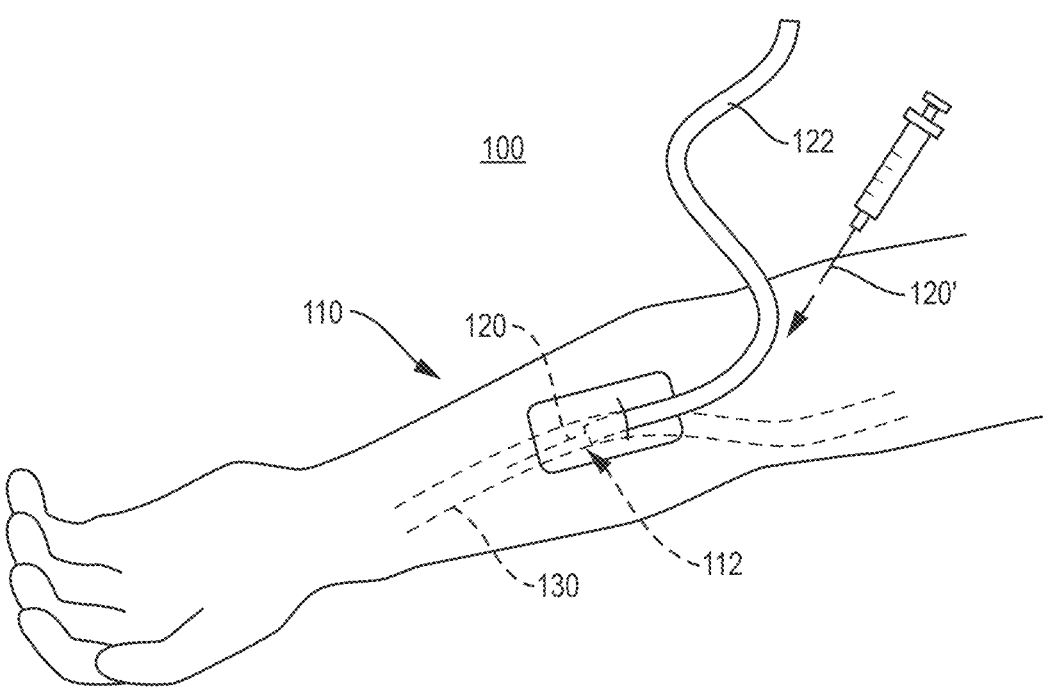
FIG. 1 is a system context diagram of a medical environment suitable for use with configurations herein.

FIG. 1 is a system context diagram of a medical environment 100 suitable for use with configurations herein. Intravenous (IV) communication is typically performed in the forearm 110 region of a patient. A needle 120 or similar rigid piercing member is inserted into a vascular structure 130 such as a vein at an insertion site 112. The needle 120 may be part of a persistent IV medication line 122 or as part of a syringe 120' for immediate insertion and withdrawal. In either case, initial introduction of the needle requires an initial piercing of the vein 130 in a manner consistent with effective fluidic communication.

Figure 2:
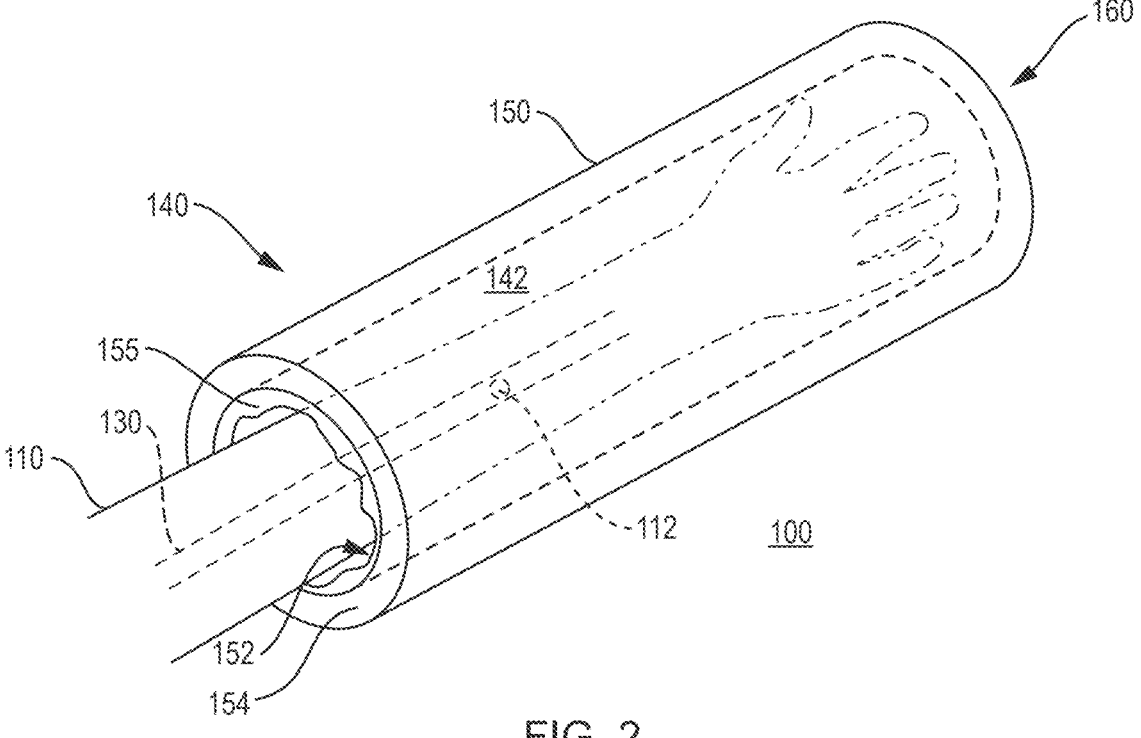
FIG. 2 shows a perspective view of the warming sleeve device in a medical context.

FIG. 2 shows a perspective view of the warming sleeve device 140 in a medical context. The device 140 includes a flexible, planar heating medium 142 adapted for encircling an appendage such as the forearm 110 for heat transfer, such that the planar heating medium 142 forms a sleeve 150 defining an interior volume 152. An opening 154 in the sleeve 150 receives the appendage into the interior volume 152 for warming the vein 130 and surrounding soft tissue. The planar heating medium 142 is activated by an electrical source, discussed further below, for energizing the heating medium 142 and warming the interior volume 152 and in turn, the vein 130 and adjacent tissue. In FIG. 2, the sleeve 150 forms an elongated shape based on a depth for receiving a length of the forearm 110 including an insertion site 112 on the forearm 110. The sleeve 150 has a length and width based on a size of an appendage to be received, such as the forearm. The length is based on accommodation of the insertion site 112, meaning to fully encapsulate the forearm 110 up to and including the insertion site 112 to ensure that the forearm 110 is within the volume 152 warmed by the sleeve 150. For a typical adult, this would be about 18 inches, and less in infants, children and adolescents. Similarly, the width is based on a circumference of the forearm 110 for maintaining a distance or contact of the sleeve for warming the forearm 110. This ranges from around 8" in adults down to around 4" for infants and children. A closure 160 at an end of the sleeve encloses the interior volume 152. A resilient, elastic panel or skirt 155 may surround the opening 154 for ensuring a snug fit and for maintaining the volume 152 somewhat sealed to avoid a convective flow that allows heat to escape to ambient air.

In an example use case, the sleeve 150 facilitates a method of pre-warming an injection site for therapeutic blood draw, including disposing the closed end sleeve over an appendage having a venous region for a percutaneous needle injection. The closed end sleeve encloses the site 112 or venous region within the warmed interior volume 152 defined by the closed end sleeve. In the example configuration, the sleeve 150 forms a substantially tubular shape closed 160 at the distal end and open at an opposed, proximate end 154 for receiving the appendage. The heating medium is configured for heating the interior volume 152 to a temperature greater than room temperature and less than a temperature that would cause thermal discomfort to a wearer. Activation of the heat source embedded in the planar heating medium 142 for a brief interval warms the interior volume 152 for enhancing a venous presence in the venous region.

Figure 3:
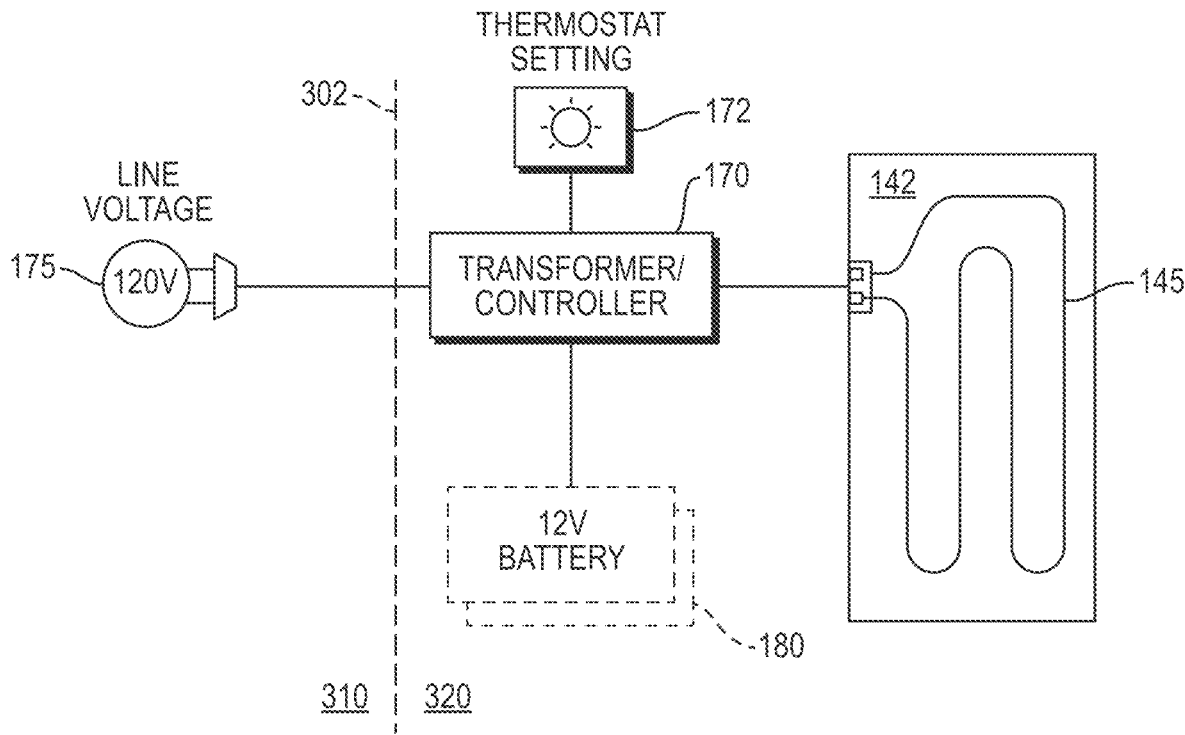
FIG. 3 shows a block diagram of the system and device disclosed herein.

FIG. 3 shows a block diagram of the system and device disclosed herein. Referring to FIGS. 2 and 3, the planar heating medium 142 may be defined by flexible textile panels having any suitable heating mechanism, however in a particular arrangement, the planar heating medium further comprises a thermal element 145 or filament disposed in an alternating manner across or adjacent to the interior surface of least one of the flexible panels, typically forming an "S" or crosshatched arrangement along the interior surface. One or both interior sides may be heated. The thermal element 145 may be a fibrous electrical conductor integrated in at least one of the flexible panels and adapted for thermal transfer to the interior volume.

An electrical supply provides a non-harmful, DC voltage via a transformer 170 for transforming and reducing a wall supply voltage 175 down to a non-oscillating, non-harmful voltage source, typically 12 or 24 VDC. In a particular arrangement, the thermal element 145 is an electrical conductor having a resistance based on achieving a temperature greater than 86° in the receptacle at a voltage of 24V. The low voltage transformer 170 in the power supply is adapted to convert electrical characteristics of a wall receptacle (typically 120 VAC) to a benign voltage and current in the fibrous electrical conductor, such that any potential shock hazard is eliminated by low voltage, low amperage and/or DC electrical operation.

In an alternate arrangement, a portable, rechargeable power source 180 (battery) may also be employed, and is readily marketed in 12V sources. Series combination therefore provides 24V. A battery powered unit is particularly effective in a large medical facility where a phlebotomist may be called around to patient rooms. Modern battery technology is rapidly evolving to provide sufficient power in a lightweight battery package to provide ample longevity with a size and weight that is not cumbersome to carry. Regardless of grid or battery power, a high voltage region 310 is effectively separated from crossing into a patient contact region 320 where low voltage prevails, as shown by dotted line 302.

As an example, the planar heating medium 142 may take the form of an alternating curved arrangement (e.g. "S" curves) alternating along a textile surface that uniformly heats the volume 152, and may be fulfilled a low cost resistance heating medium. An absence of crossover or crosshatching (e.g. "grid") arrangement avoids potential short circuits where electrical conductors cross. A variable thermostatic, or fixed thermistor control 172 may be established, as any gentle warming in excess of around 86 degrees will enhance vein receptibility to needles, and of course should not (and need not) heat to an uncomfortable level.

Figure 4:
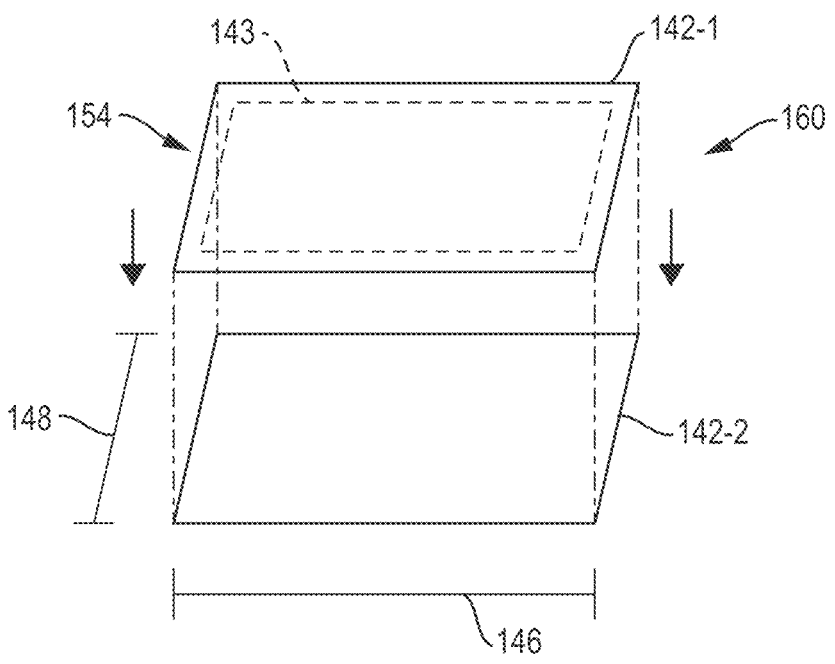
FIG. 4 shows an exploded view of an example configuration of the warming sleeve device of FIG. 2.

FIG. 4 shows an exploded view of an example configuration of the warming sleeve device of FIG. 2. FIG. 4 shows the particular configuration of the phlebotomy warming sleeve 150 constructed as opposed panels of the flexible heating medium 142-1 . . . 142-2 for use with various patient including children and adults via different sizes. The length 146 and width 148 are generally based on the patient forearm size, as indicated above. Any suitable width may be employed, however it is expected that a width of about 4 inches or less for infants and toddlers, 6 inches for children up to around teens or adolescence, and about 8 inches for fully grown adults. Enhancement of blood vessel features begins occurring with any degree of warming, however it is proposed that the patient's forearm occupy the warming sleeve for about 10-15 minutes at a temperature of around 100°-103° to provide maximum effect without discomfort from excessive temperature.

The opposed panels 142-1 . . . 142-2 each define a surface and have a substantially equal area and an aligned perimeter, and may be fulfilled by rectangular textile panels such that a seam 143 or threaded attachment extends around three of four sides of the textile panels, thus forming the closed end 160 and leaving an open width on the fourth side to define the proximate side 154 opening for forearm insertion.

Figure 5:
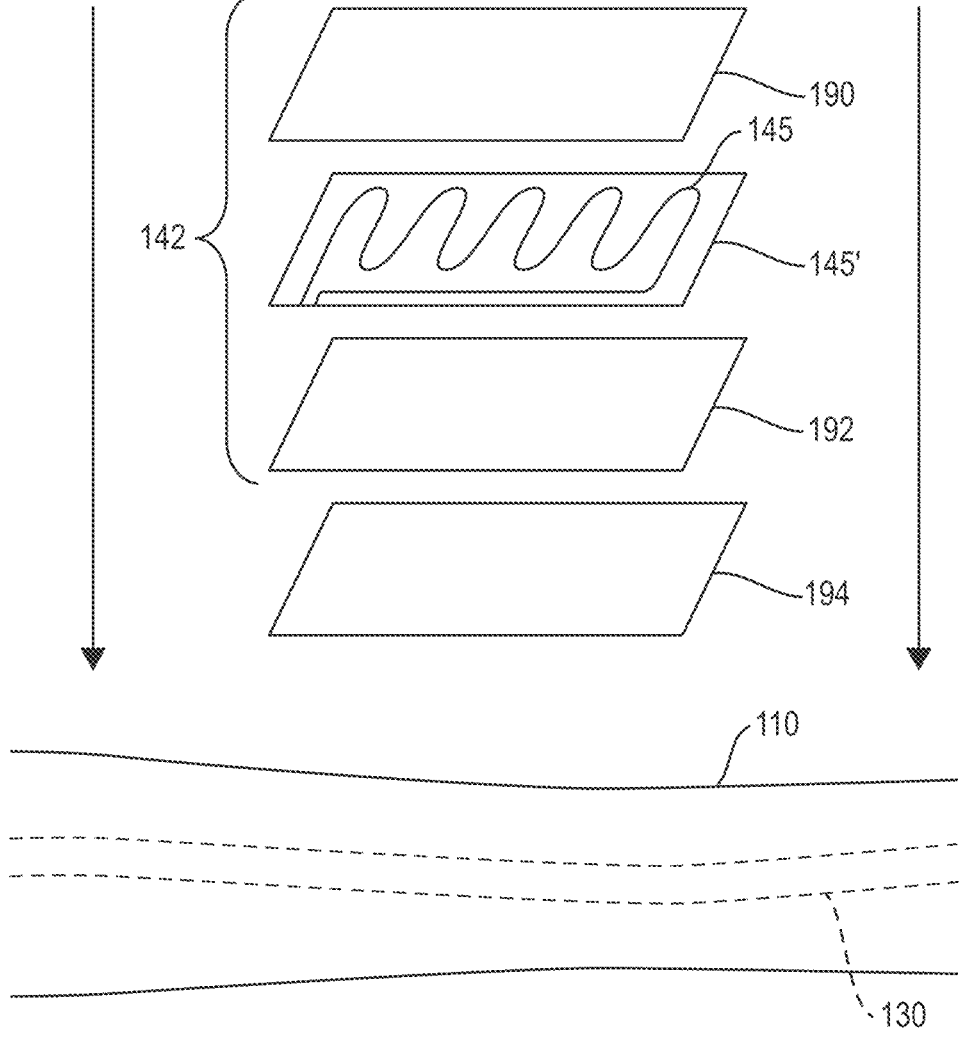
FIG. 5 shows an exploded view of a flexible, planar heating medium as used in the device of FIGS. 2-4.

FIG. 5 shows an exploded view of a flexible, planar heating medium 142 as used in the device of FIGS. 2-4. Referring to FIGS. 2-5, construction of the planar heating medium 142 takes the form of a flexible planar material including a textile base 190, a linear thermal (heating) element 145 adhered to the textile base 190, such that the linear thermal element has an electrical resistance for heat generation and a traversal pattern across the textile base. The linear thermal element 145 may optionally be adhered or integrated to a flexible substrate 145' for positioning and/or assembly. A second layer 192 of a textile or insulating material may encapsulate the linear thermal element 145 to buffer the forearm 110 from direct contact with the thermal element, thus defining the interior surface of the sleeve 150. This layered structure forms the example planar heating medium 142 that is joined as in FIG. 4 to form the sleeve 150. A protective or single-use sanitary layer 194 may further intervene between the direct forearm skin contact. The layer 194 is likely better served by a plastic liner, glove or pouch fitted between the forearm 110 and the sleeve 150, rather than as a permanent surface attached to the planar heating medium 142. This entire assembly forms one panel of the sleeve 150 for warming the vein 130 of the forearm 110.

Figure 6:
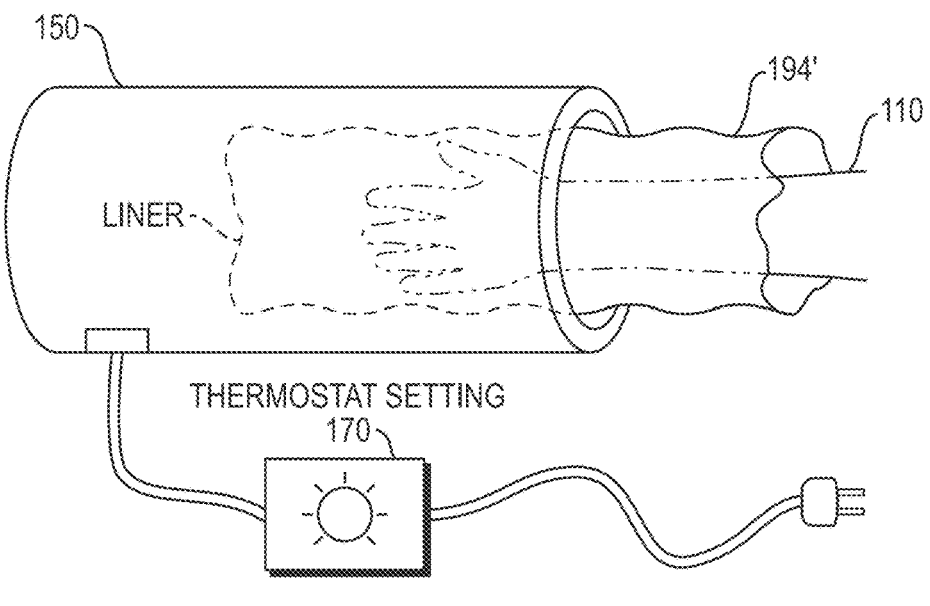
FIG. 6 shows the device of FIGS. 2-5 in use.

FIG. 6 shows the device of FIGS. 2-5 in use. A complete phlebotomy aid system as presented herein provides the sleeve 150 for receiving a human forearm 110 into a receptacle defined by joining, wrapping or otherwise forming the planar heating medium 142. The planar heating medium 142 forms the sleeve 150 as described above, and a liner 194' has a size based on an interior volume of the receptacle for insertion thereof to prevent interpatient contamination. The liner further comprises a thermally conductive material (or at least non-insulating) configured for conducting heat from the thermal element to the volume 152 defined by the receptacle, and may simply be a lightweight plastic, paper or latex sheath that prevents individual patient contact with the interior of the sleeve 150. The disposable, single use liner is simply discarded and a successive patient provided a fresh, sterilized liner.

Figure 7A:
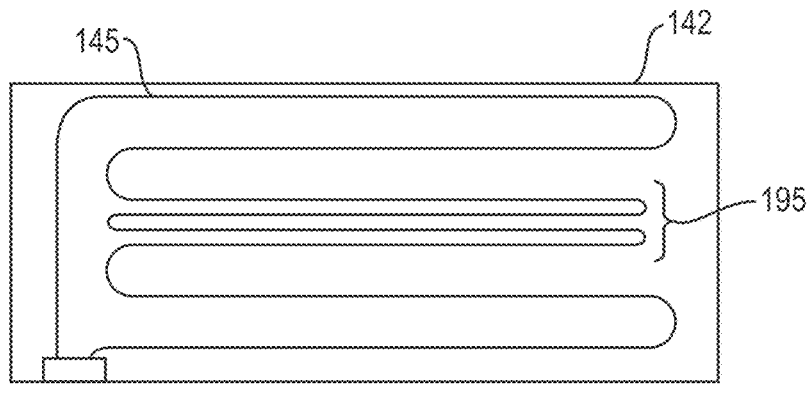
FIGS. 7A and 7B show a path of a liner thermal element used in FIGS. 2-6.
Figure 7B:
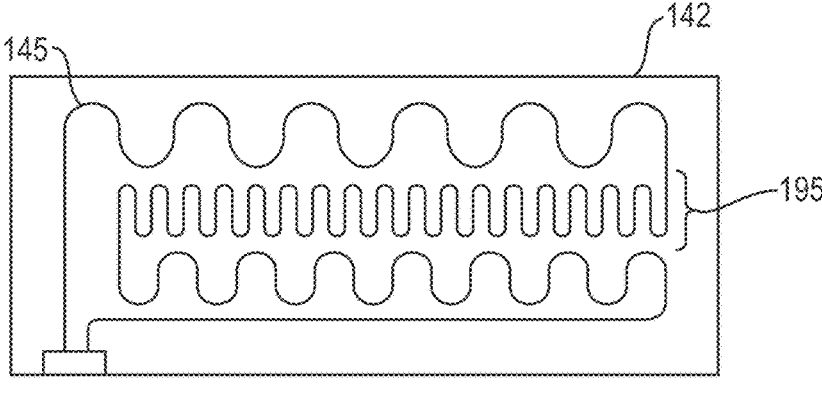

FIGS. 7A and 7B show a path of a linear thermal element used in FIGS. 2-6. In the planar heating medium 142, the disclosed approach traverses the linear thermal element across the sleeve 150. The linear thermal element traverses a path across the textile base 190, such that the path defines a heating zone 195 based on an expected location of a vein 130 in the forearm. Although the linear thermal element 145 could be evenly distributed across the surface, concentration of the linear thermal element 145 in the heating zone 195 can focus more heat onto the vein 130. Accordingly, successive passes of the linear thermal element 145 may be disposed at a closer distance in the heating zone 195 for focusing heat on location of the vein 130. FIG. 7A shows longitudinal passes of narrower width in the heating zone 195, while FIG. 7B shows increased width oscillations spanning the shorter dimension of the sleeve 150.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medical device, comprising:
a flexible, planar heating medium adapted for encircling an appendage for heat transfer, the planar heating medium forming a sleeve defining an interior volume;
a textile base;
the planar heating medium including a linear thermal element adhered to the textile base, the linear thermal element responsive to electricity for heat generation across the textile base,
the linear thermal element traversing a path across the textile base, the path defining a heating zone based on an expected location of a vein in the appendage; the linear thermal element disposed at a distance in the heating zone for focusing heat on the expected location of the vein, the heating zone, the heating zone including a longitudinal center along at least one panel of the textile base and the heating zone generating greater heat than the planar heating medium outside the heating zone;
an opening in the sleeve for receiving an appendage into the interior volume for warming; and
an electrical source for energizing the heating medium for warming the interior volume.

2. The device of claim 1 wherein the sleeve forms an elongated shape based on a depth for receiving a length of a forearm including an epidermal insertion site on the appendage.

3. The device of claim 1 wherein the sleeve has a length and width based on a size of an appendage to be received,
the length based on a location of an epidermal insertion site for receiving the appendage at a depth based on the location;
the width based on a circumference of the appendage for maintaining a distance or contact of the sleeve for warming the appendage; and
a closure at an end of the sleeve for enclosing the interior volume.

4. The device of claim 1 wherein the sleeve forms a tubular shape, the tubular shape closed at a distal end and open at an opposed, proximate end for receiving the appendage; the
heating medium configured for heating the interior volume.

5. The device of claim 1 wherein the electrical supply provides a DC voltage.

6. The device of claim 1 wherein the power supply includes a transformer for transforming and reducing a wall supply voltage down to a non-oscillating, non-harmful voltage source.

7. The device of claim 1 wherein the flexible planar material includes:
an insulating material between the linear thermal element and the textile base.

8. The device of claim 1, wherein the textile base further comprises a pair of opposed rectangular panels joined around three sides of an outer perimeter of the rectangle; and
the linear thermal element traverses an interior surface of at least one textile base of the opposed rectangular panels on an interior side facing the interior volume,
the heating zone having a greater concentration of the linear thermal element then the textile base outside the heating zone,
the heating zone occupying at least a middle portion of at least one interior surface, the middle portion defined by a region extending longitudinally across the rectangular panel and having equal regions of textile base aligned adjacent and outside the heating zone.

9. A phlebotomy aid system, comprising:
an elongated flexible sleeve having an opening, the flexible sleeve defined by a textile base and having a receptacle adapted for receiving a human forearm;
a liner having a size based on an interior of the receptacle for insertion thereof;
a linear thermal element attached to the sleeve for heating the receptacle, the linear thermal element adhered to the textile base, the linear thermal element responsive to electricity for heat generation across the textile base;
the linear thermal element traversing a path across the textile base, the path defining a heating zone based on an expected location of a vein in the appendage; the linear thermal element disposed at a distance in the heating zone for focusing heat on the expected location of the vein, the heating zone, the heating zone including a longitudinal center along at least one panel of the textile base and the heating zone generating greater heat than the planar heating medium outside the heating zone; and a power supply connected to the thermal element for energizing the thermal element.

10. The system of claim 9 wherein the liner further comprises a thermally conductive material configured for conducting heat from the thermal element to the receptacle.

11. The system of claim 10 wherein the elongated sleeve has a length based on a distance from an elbow of the human forearm to a fingertip region.

12. The system of claim 11 wherein the flexible sleeve further comprises:

opposed flexible panels attached at a seam extending partially around a perimeter of the flexible panels;

each of the flexible panels having a width based on a circumference of the human appendage; and an opening defined by an absence of the seam for defining the opening.

13. A phlebotomy aid device, comprising:

an elongated flexible sleeve having an opening;

the flexible sleeve defining a receptacle adapted for receiving a human forearm;

a linear thermal element attached to the sleeve for heating the receptacle;

the linear thermal element adhered to the textile base, the linear thermal element responsive to electricity for heat generation across the textile base;

the linear thermal element traversing a path across the textile base, the path defining a heating zone based on an expected location of a vein in the appendage; the linear thermal element disposed at a distance in the heating zone for focusing heat on the expected location of the vein, the heating zone, the heating zone including a longitudinal center along at least one panel of the textile base and the heating zone generating greater heat than the planar heating medium outside the heating zone; and a power supply connected to the thermal element for energizing the thermal element.

14. The device of claim 13 wherein the flexible sleeve further comprises:

opposed flexible panels attached at a seam extending partially around a perimeter of the flexible panels; and an opening defined by an absence of the seam for defining the opening.

15. The device of claim 14 wherein the flexible panels each define a surface and have a substantially equal area and an aligned perimeter.

16. The device of claim 14 wherein the flexible panels further comprise rectangular textile panels and the seam is a threaded seam extending around three of four sides of the textile panels; and a fourth side of each of the flexible panels defining the opening.

17. The device of claim 13 wherein the thermal element further comprises a heating filament disposed in an alternately curving, cyclic path across the surface of least one of the flexible panels.

18. The device of claim 17 wherein the thermal element further comprises a fibrous electrical conductor integrated in at least one of the flexible panels and adapted for thermal transfer to the receptacle.

19. The device of claim 18 further comprising a transformer in the power supply, the transformer adapted to convert household 120 volts of a wall receptacle to a DC (direct current) voltage and current in the fibrous electrical conductor.

20. The device of claim 13 wherein the thermal element is an electrical conductor having a resistance based on achieving a temperature greater than 86° in the receptacle at a voltage of 24V.

* * * * *